United States Patent
Hess et al.

(10) Patent No.: US 6,592,582 B2
(45) Date of Patent: Jul. 15, 2003

(54) VESSEL HARVESTING RETRACTOR WITH ELECTROSURGICAL PLUNGER

(75) Inventors: Christopher J. Hess, Lebanon, OH (US); Michael F. Clem, Maineville, OH (US); Gary W. Knight, West Chester, OH (US); Rudolph H. Nobis, Mason, OH (US); Dale R. Schulze, Lebanon, OH (US)

(73) Assignee: Ethicon, Inc., Somerville, NJ (US)

( * ) Notice: Subject to any disclaimer, the term of this patent is extended or adjusted under 35 U.S.C. 154(b) by 67 days.

(21) Appl. No.: 09/966,858

(22) Filed: Sep. 28, 2001

(65) Prior Publication Data

US 2003/0065323 A1 Apr. 3, 2003

(51) Int. Cl.⁷ ............................................... A61B 18/18
(52) U.S. Cl. ........................................... 606/49; 606/41
(58) Field of Search ................................ 600/564, 565, 600/566, 567, 568; 606/41, 42, 43, 44, 45, 46, 47, 48, 49, 50

(56) References Cited

U.S. PATENT DOCUMENTS

| | | | |
|---|---|---|---|
| 5,366,476 A | * | 11/1994 | Noda ........................ 606/206 |
| 5,591,183 A | | 1/1997 | Chin |
| 5,593,418 A | | 1/1997 | Mollenauer |
| 5,601,581 A | | 2/1997 | Fogarty et al. |
| 5,667,480 A | | 9/1997 | Knight et al. |
| 5,695,514 A | | 12/1997 | Chin |
| 5,722,934 A | | 3/1998 | Knight et al. |
| 5,725,479 A | | 3/1998 | Knight et al. |
| 5,730,748 A | | 3/1998 | Fogarty et al. |
| 5,797,947 A | | 8/1998 | Mollenauer |
| 5,817,013 A | | 10/1998 | Ginn et al. |
| 5,836,945 A | | 11/1998 | Perkins |
| 5,853,417 A | | 12/1998 | Fogarty et al. |
| RE36,043 E | | 1/1999 | Knighton |
| 5,873,889 A | | 2/1999 | Chin |
| 5,876,413 A | | 3/1999 | Fogarty et al. |
| 5,891,140 A | | 4/1999 | Ginn et al. |
| 5,899,913 A | | 5/1999 | Fogarty et al. |
| 5,902,316 A | | 5/1999 | Mollenauer |
| 5,916,233 A | | 6/1999 | Chin |
| 5,922,004 A | | 7/1999 | DuBois |
| 5,928,138 A | | 7/1999 | Knight et al. |
| 5,938,680 A | | 8/1999 | Ginn |
| 5,968,065 A | | 10/1999 | Chin |
| 5,968,066 A | | 10/1999 | Fogarty et al. |
| 5,970,982 A | | 10/1999 | Perkins |
| 5,972,010 A | | 10/1999 | Taheri |
| 5,976,168 A | | 11/1999 | Chin |
| 5,980,549 A | | 11/1999 | Chin |
| 5,984,937 A | | 11/1999 | Morse et al. |
| 6,019,771 A | | 2/2000 | Bennett et al. |
| 6,022,313 A | | 2/2000 | Ginn et al. |

(List continued on next page.)

FOREIGN PATENT DOCUMENTS

| | | |
|---|---|---|
| EP | 0 979 635 A2 | 2/2000 |
| WO | WO 99/66842 | 12/1999 |
| WO | WO 00/15116 | 3/2000 |

*Primary Examiner*—Roy D. Gibson
*Assistant Examiner*—Aaron Roane (57) ABSTRACT

An endoscopic device including a shaft having a lumen for insertion of an endoscope therethrough, a transparent headpiece defining a workspace and disposed at a distal end of the shaft, a handle disposed at a proximal end of the shaft, a plunger disposed at the distal end of the shaft and movable between a retracted and extended position, wherein in the extended position the plunger interacts with at least a portion of the headpiece to capture a vessel therebetweeen, an actuator for moving the plunger between the retracted and extended positions, and a ligator for cauterizing the vessel captured between the plunger and the portion of the headpiece.

17 Claims, 7 Drawing Sheets

U.S. PATENT DOCUMENTS

| | | |
|---|---|---|
| 6,036,713 A | 3/2000 | Kieturakis |
| 6,036,714 A | 3/2000 | Chin |
| 6,042,538 A | 3/2000 | Puskas |
| 6,059,802 A | 5/2000 | Ginn |
| 6,068,639 A | 5/2000 | Fogarty et al. |
| 6,071,232 A | 6/2000 | Knighton et al. |
| 6,080,102 A * | 6/2000 | Konou et al. ............... 600/114 |
| 6,120,434 A | 9/2000 | Kimura et al. |
| 6,139,489 A | 10/2000 | Wampler et al. |

* cited by examiner

VESSEL HARVESTING RETRACTOR WITH ELECTROSURGICAL PLUNGER

FIELD OF THE INVENTION

The present invention relates generally to vessel harvesting and in particular to an improvement over existing endoscopic vessel harvesting techniques and devices.

BACKGROUND OF THE INVENTION

Endoscopic harvesting of vessels is well known in the surgical field and has been the subject of a great deal of recent technological advancement. Typically, the harvesting of vessels is performed so that the vessels can then be used for procedures such as Cardio Artery Bypass Grafting (CABG). In this procedure the saphenous veins of the legs are harvested for subsequent use in the CABG surgery.

Devices and methods for such vessel harvesting are well known and have been described in numerous publications including U.S. Pat. No. 5,667,480 issued Sep. 16, 1997 and U.S. Pat. No. 5,722,934 issued Mar. 3, 1998 to Knight et al, both of which are incorporated herein by their reference. The devices and methods of these patents are briefly described below.

In the traditional harvesting devices, there is provided a hollow shaft connected to a concave headpiece located at the distal end of the shaft which provides a workspace. An endoscope is typically inserted in the shaft so that the surgeon may view workspace. The leading edge of the headpiece is used for dissecting the vessel from the surrounding tissue. The device may also have guide rails located on the underside of the device which allow for the entry of other devices such as dissectors, ligation tools, and cutting tools into the workspace.

The traditional method for removal of a vessel section is as follows. Initially an incision is made and the vessel is located. Then, the vessel is dissected form the surrounding tissue using the leading edge of the headpiece of the device to separate the tissue from the vessel. At this time there is sufficient workspace created around the vessel so that other instruments can be inserted into the incision via the guide rails located on the underside of the device. These instruments include ligation tools for securing side branch vessels, a vessel dissector for performing a more complete dissection of the vessel, which is to be removed, and laproscopic scissors for the transection of both the side branch vessels and the vessel which is to be removed.

Of the known devices and methods for removal of vessels there remains one constant problem. The problem is that to perform each an every one of the side branch ligation and transactions, extra tools must be inserted along the guide rails of the device through the original incision. Often times this means that to perform a single transection of a side branch vessel three tools must be inserted in succession into the body. The various tools include, a dissector to dissect the side branch from the surrounding tissue, a ligation tool to clamp the side branch vessel and the vessel to be removed, and a cutting tool to perform the transection. Additionally, the harvesting device remains in the body throughout the procedure.

This requirement of inserting the tools in succession and exchanging one tool for another to perform each step of the operation requires extra time, this in turn can be a drain on the individual surgeons resources. Further, because of this increased amount of time, which the surgeon requires to perform the operation, the stress on the patient is increased. Minimization of patient stress is naturally a concern during any surgical procedure. Therefore, the elimination of some or all of the time extending tool exchanges would greatly benefit not only the patient but the surgeon as well.

SUMMARY OF THE INVNETION

The present invention is directed to solving the shortcomings of known vessel harvesting devices, by providing a superior vessel harvesting device, promoting efficient removal of vessels, and limiting the stress on patients. The objects of the present invention are the minimization of the tool exchanges, increased efficiency of operation, minimization of patient stress, and increased ease of the overall harvest operation. Further, the present invention pertains to a device having a means for capturing side branch vessels so that they may be ligated and transected.

Accordingly a vessel harvesting device is provided. The endoscopic device comprises a shaft having a lumen for insertion of an endoscope therethrough, a headpiece defining a workspace and disposed at a distal end of the shaft, a handle disposed at a proximal end of the shaft, a plunger disposed at the distal end of the shaft and movable between a retracted and extended position, wherein in the extended position the plunger interacts with at least a portion of the headpiece to capture a vessel there between, an actuation means for moving the plunger between the retracted and extended positions, and a ligation means for cauterizing the vessel captured between the plunger and the portion of the headpiece.

The vessel harvesting device preferably comprises a transection means for transecting the cauterized vessel, wherein the portion of the headpiece comprises a hook projecting into the workspace.

The headpiece preferably comprises side projections extending from an edge of the headpiece and projecting towards the plunger of the headpiece, the side projections facilitating the positioning of the vessel for capture.

The ligation means preferably comprises the plunger having at least two electrodes of opposite polarity separated by at least one dielectric layer, the electrodes being energized with RF energy to cauterize the captured vessel.

The transection means preferably comprises the plunger having an extendable knife separated from each of the at least two electrodes by a dielectric layer, wherein the at least two electrodes comprises a first and second electrode and one of the first and second electrodes is a knife separated from the other electrode by at least one dielectric layer.

The portion of the headpiece preferably comprises a slidable hook projecting into the workspace, movable from an extended to a retracted position, wherein the hook interacts with the plunger to capture the side branch when in the extended position.

The vessel harvesting device further preferably comprises a control rod actuation means for moving the slidable hook between the extended and retracted positions, wherein the control rod actuation means comprises a flexible control rod operably connected to the slidable hook for sliding the slidable hook between the extended and retracted positions, the control rod having an extension stop which limits the travel of the slidable hook and also having a capturing means which prevents the slidable hook and the control rod from entering the workspace, and wherein the control rod is formed of a flexible material conforming to the shape of the headpiece while transitioning from the retracted to the extended position and maintaining its conformance with the headpiece when in the extended position.

Also provided is a method of removing a vessel utilizing the above-described device. The method of harvesting a vessel comprising the steps of providing a vessel harvesting device comprising a shaft having a lumen for insertion of an endoscope therethrough, a transparent headpiece defining a workspace and disposed at a distal end of the shaft, a handle disposed at a proximal end of the shaft, a plunger disposed at the distal end of the shaft and movable between a retracted and extended position, wherein in the extended position the plunger interacts with at least a portion of the headpiece to capture a vessel therebetween, an actuation means for moving the plunger between the retracted and extended positions, a ligation means for cauterizing the side branch, and a transection means for transecting the cauterized side branch, locating a vessel to be harvested, making an incision to expose the vessel, inserting the vessel harvesting device into the patient through the incision, dissecting the vessel from the surrounding tissue with the vessel harvesting device to expose a side branch of the vessel, actuating the plunger in the distal direction to capture the side branch between the plunger and the portion of the headpiece, applying RF energy to cauterize the captured side branch, transecting the cauterized side branch using the transection means, ligating and transecting the vessel, and removing the vessel.

The step of ligating the side branch preferably comprises applying RF energy to the side branch using first and second electrodes, wherein the first and second electrodes are of different polarity and are housed in the plunger.

The step of transecting the side branch preferably comprises extending a knife housed in the plunger towards the distal end of the device.

The step of capturing preferably comprises placing the headpiece over the side branch and extending the plunger in the distal direction to allow the side branch to be compressed between the plunger and the portion of the headpiece.

The step of transecting the side branch preferably comprises advancing a knife housed in the lower jaw towards the distal end of the device subsequent to the ligation of the side branch vessel.

The step of actuating preferably comprises extending a slidable hook in the distal direction prior to extension of the plunger.

This use of the plunger and the ligation and transection means located therein limits the number of tools which must be inserted into the incision. Further, by having the ligation and transection means located in the plunger the procedure is more easily performed, and with a minimum of stress to the patient and in a decreased amount of time.

DETAILED DESCRIPTION OF THE PREFERRED EMBODIMENT

Figure 1:
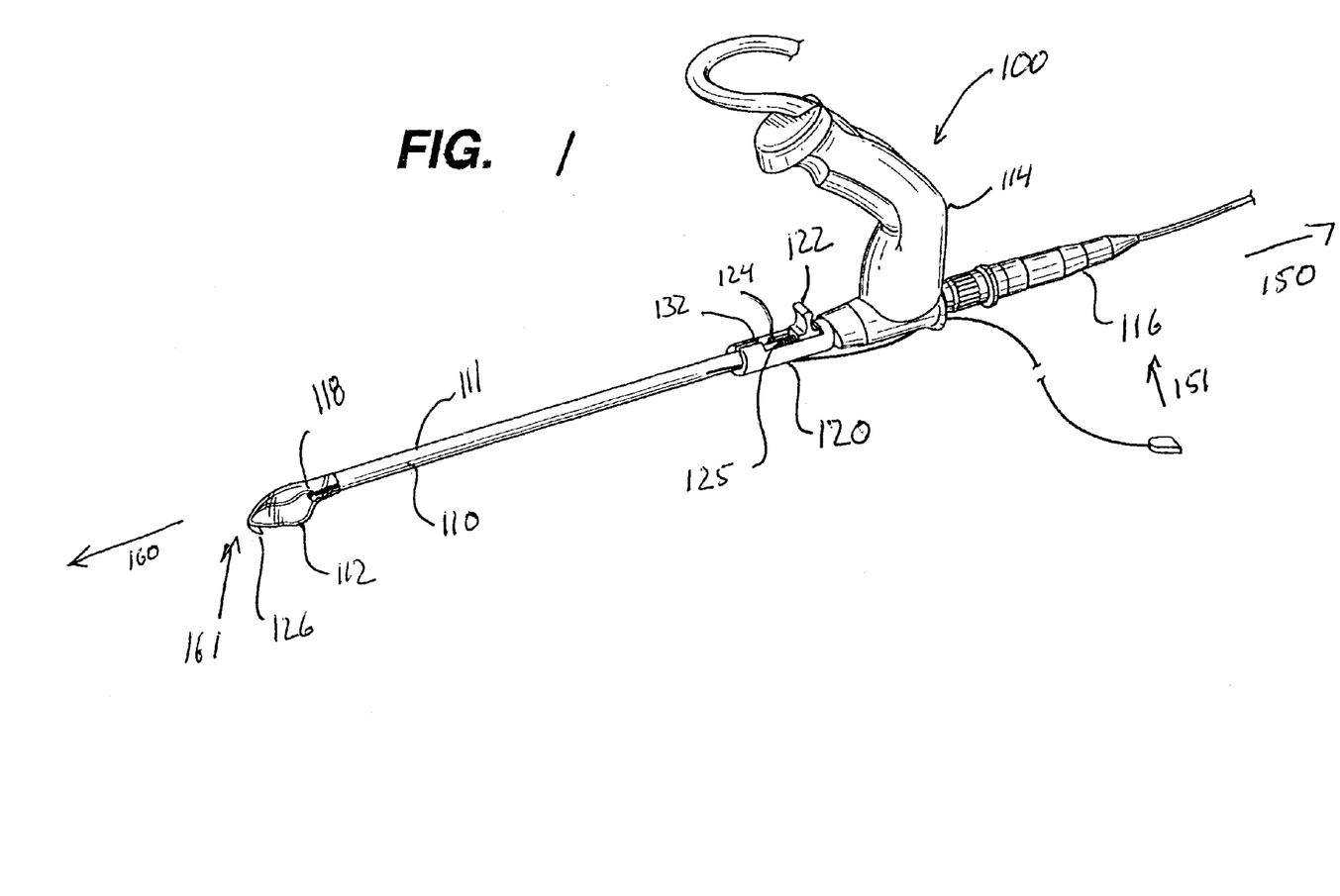
FIG. 1 illustrates a perspective view of preferred implementation of an endoscopic vessel harvesting device of the present invention.

Referring now to FIG. 1, a preferred implementation of an endoscopic vessel harvesting device (EVH) for the removal of vessels from a body is illustrated therein, generally referred to by reference number 100. Specifically, the EVH 100 is often used for the removal of the saphenous vein from the leg of a patient undergoing a CABG operation. The embodiments discussed herein are directed to the removal of such saphenous veins, however, it should be noted that they are not limited to the removal of saphenous veins and could be utilized for the removal of any vessel from a patient. As described above, traditional procedures for removing the saphenous vein required the exchange of various tools multiple times for each side branch ligation and transection.

Accordingly, the EVH 100 is provided to overcome the disadvantages of the prior art. The vessel harvesting device (EVH) 100 is comprised of a shaft 110, the shaft is used to house an endoscope 116 inserted therein. The shaft 110 is preferably formed of a medical grade material, such as stainless steel.

Figure 2:
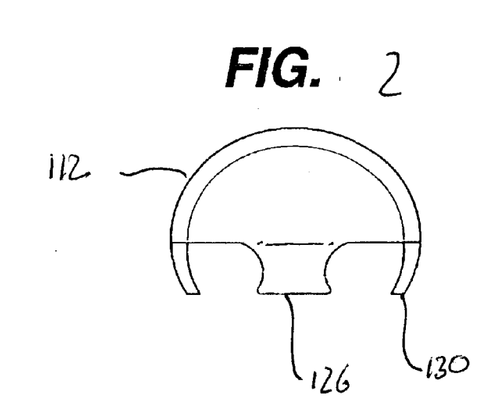
FIG. 2 illustrates an enlarged front view of the headpiece of the endoscopic vessel harvesting device of FIG. 1.
Figure 3:
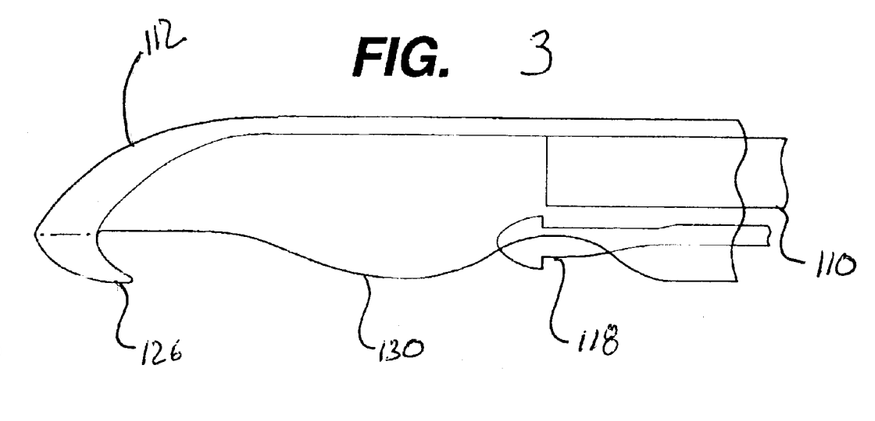
FIG. 3 illustrates an enlarged side view of the headpiece of the endoscopic harvesting device of FIG. 1
Figure 4:
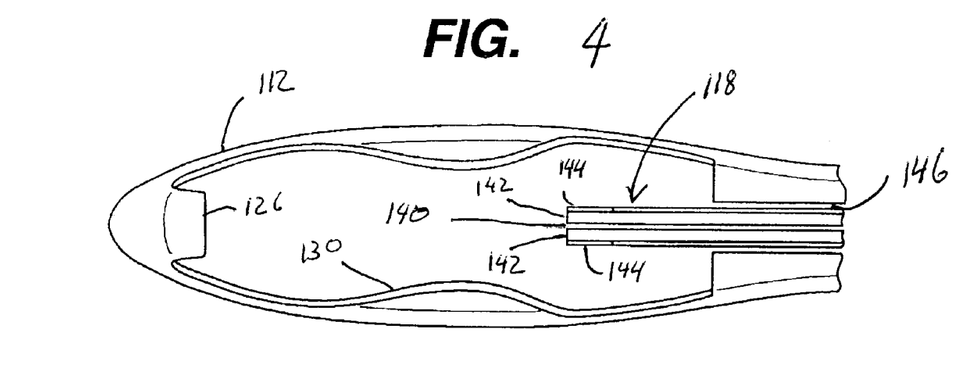
FIG. 4 illustrates an enlarged bottom view of the headpiece of the endoscopic harvesting device of FIG. 1.

On the distal end 161 of the shaft 110 there is disposed a headpiece 112. The headpiece 112 is preferably formed of a medical grade transparent material such as, polycarbonate. The headpiece 112 is used for dissection of a vessel from the surrounding tissue. The headpiece 112 defines a workspace 127, which can be viewed through an endoscope 116 inserted into the shaft 110 to which the headpiece 112 is attached. Referring now to FIGS. 2–4, on a distal end 161 of the headpiece 112 there is preferably located a hook 126. The hook 126 is angled toward the proximate end 151 of the EVH 100. As will be discussed below, the hook 126 assists in the dissection of vessels and is used in the compression, ligation and transection of the dissected vessel. On the sides of the headpiece 112 there are extensions 130 which extend downward and towards the center of the device, as can be seen in FIG. 4. As will be discussed below, these extensions 130 assist in the dissection of vessels.

Referring back to FIG. 1, on a proximal end 151 of the EVH 100 there is disposed a handle 114. The handle 114 is preferably formed of a thermoplastic. The handle is used to manipulate the EVH 100. The handle 114 also preferably provides an insertion point for.the endoscope and may house various controls.

Referring to FIG. 4 a plunger 118 is disposed on the distal end 161 of shaft 110 and is movable from a retracted position to an extended position within the workspace 127. The plunger 118 interacts with a portion of the headpiece 112. In a first variation the portion is an integrally formed hook 126. The plunger 118 is extendable in the direction of hook 126, and this movement facilitates the capture of vessels between the plunger 118 and the hook 126.

Figure 7:
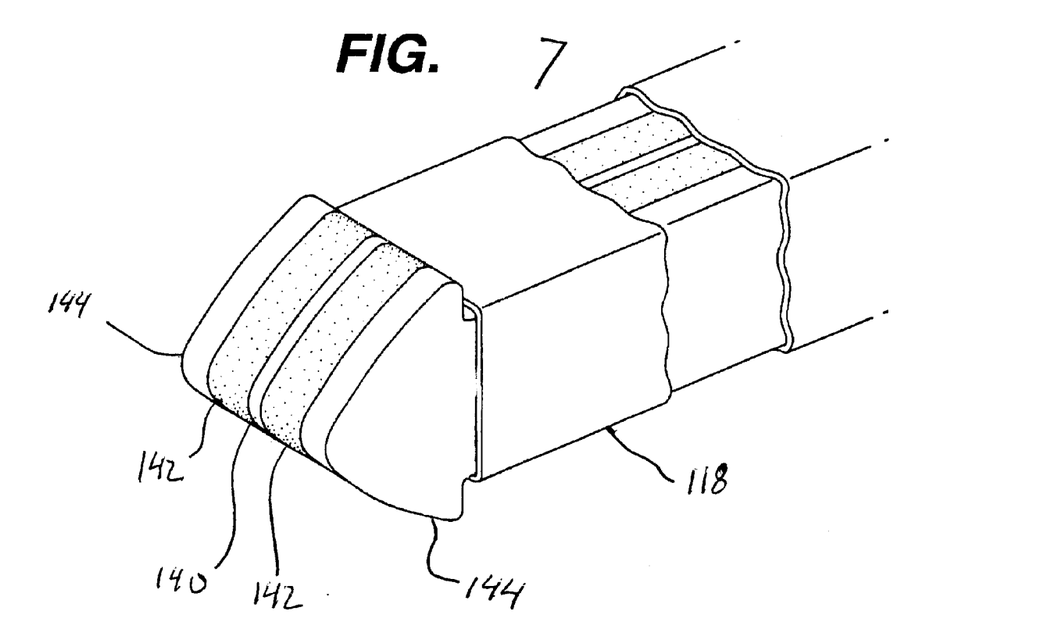
FIG. 7 illustrates an enlarged view of a plunger with the knife retracted.

The EVH 100 preferably comprises a ligation means. The ligation means is preferably located on the plunger 118 as shown in FIG. 7. The ligation means is preferably a pair of electrodes 144 which can be energized with RF energy to cauterize a vessel captured between the plunger 118 and the hook 126.

Figure 8:
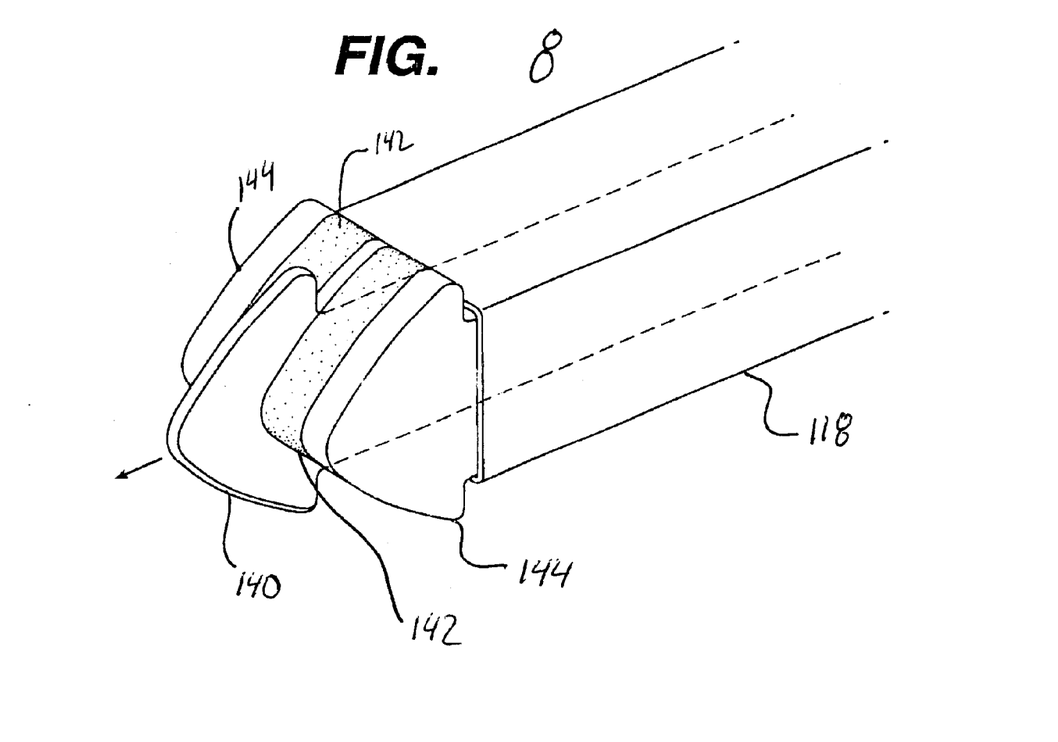
FIG. 8 illustrates an enlarged view of a plunger with the knife extended.

Additionally, the EVH 100 preferably comprises a transection means. The transection means is preferably housed in the plunger 118 as shown in FIG. 8. The preferred transection means is a knife 140 housed between the electrodes 144. The knife 140 is used to cut a vessel captured between the plunger 118 and the hook 126 and cauterized by the electrodes 144.

The plunger 118 is preferably formed of two electrodes 144 of opposite polarities, separated from one another by at least one insulator 142, as shown in FIG. 7. The electrodes are preferably formed of a medical grade stainless steel and are electrically connected to an RF generator as is known in the art. The electrodes are energized by either controls (not shown) located in the handle 114, or by a foot pedal (also not shown) as is commonly used in the art, and shown in FIG. 1. As shown in FIG. 7 it is preferable that a knife 140 is disposed between the two insulators 142, and the electrodes 144 are separated from the insulators 142 to isolate them from each other electrically and/or the knife 140. The knife 140 is formed of a medical grade material, such as a stainless steel hardened to maintain a sharp edge for the life of the device. The insulators 142 are preferable formed of a medical grade insulating material such as, but not limited to polycarbonate and polyethylene, in of a thickness in the range of about 1–2 mm.

The electrodes are preferably offset from one another by the insulators 142 and the knife 140 a distance 2.5 mm. This minimizes the collateral damage done to the vessel and the surrounding tissue.

In an alternative implementation of the invention the knife 140 can serve as an electrode of one polarity and the two electrodes 144 can serve as a single electrode of a second polarity.

Figure 9:
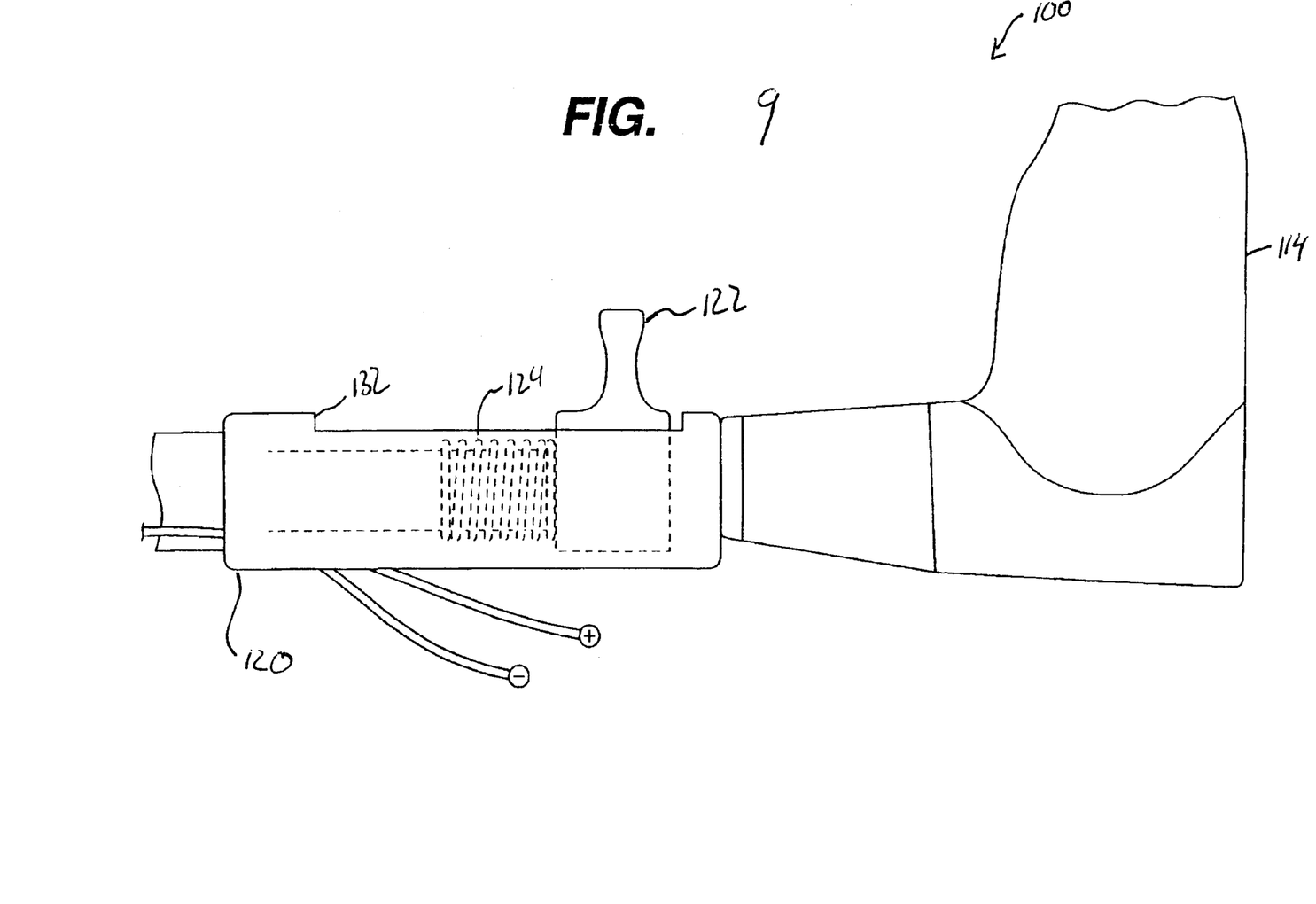
FIG. 9 illustrates a cross sectional view of the actuator and handle of the device of FIG. 1.

Referring now to FIG. 9, the EVH 100 also includes an actuator 120 for the actuation of the plunger 118. The actuator 120 is preferably disposed on the proximal end 151 of the shaft 110. The actuator 120 is comprised of a control knob 122, a biasing means 124, a carriage 125 (shown in FIGS. 14–16), and a stop 132. The control knob 122 is connected to the plunger 118. The biasing means 124 may be a spring 124, as shown in FIG. 9, and acts upon the stop 132 to return the control knob 122 to a certain position.

As shown in FIG. 1, extending from the headpiece 112 to the actuator 120 and covering the shaft 110 is a plastic sheath 111 formed preferably of a polycarbonate. Referring now to FIG. 4 the sheath 111, as shown in FIG. 1, provides a housing for a slot 146 in which the plunger 118 is slidably housed, and may also provide a second slot (not shown) for a control rod 244, when used with a slidable hook 226 configuration, as shown in FIG. 14, and discussed below.

The plunger 118 extends from the actuator 120 to the headpiece 112, and is housed in a slot 146. The control knob 122, in connection with a carriage 125, is used to move the plunger 118 from a retracted to an extended position. FIG. 3 shows the plunger 118 in a retracted position.

Figure 14:
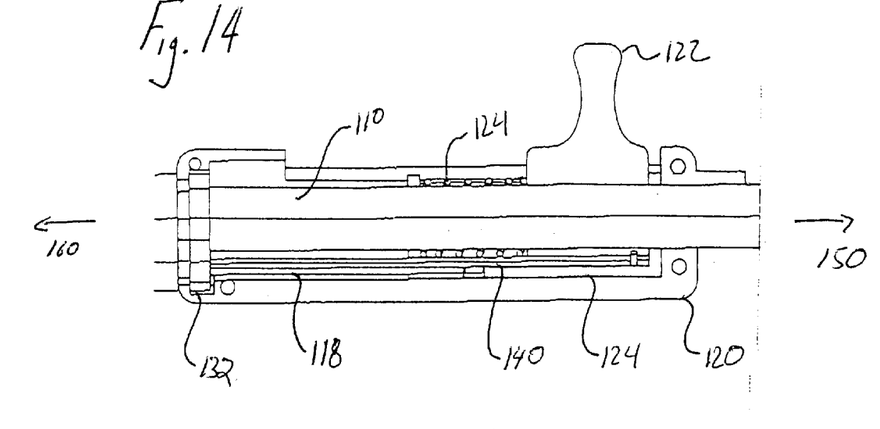
FIG. 14 illustrates an enlarged side view of the actuator of FIG. 1, showing the position of the components of the actuator when the plunger is retracted.
Figure 15:
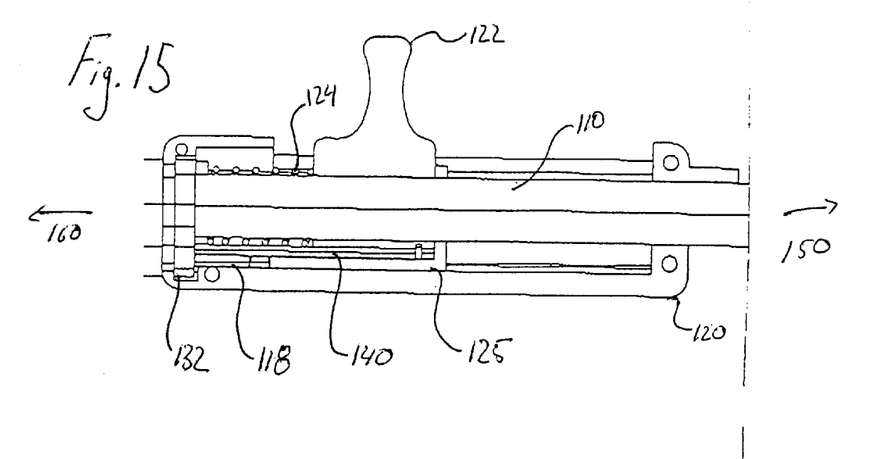
FIG. 15 illustrates an enlarged side view of the actuator of FIG. 1, showing the position of the components of the actuator when the plunger is extended.
Figure 16:
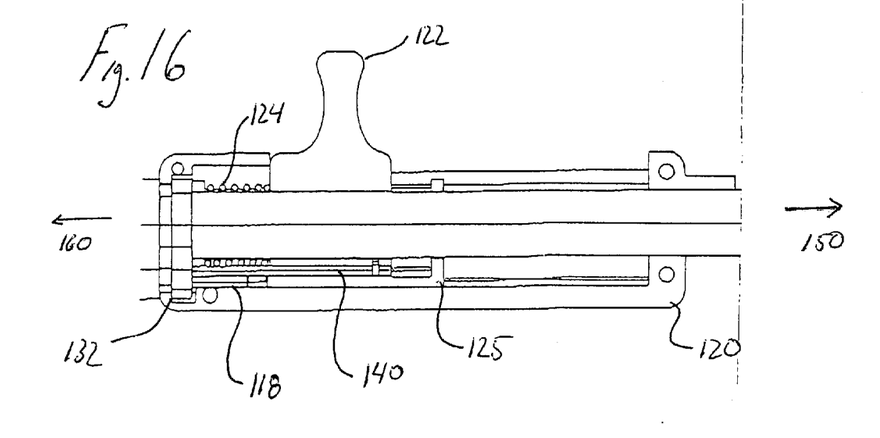
FIG. 16 illustrates an enlarged side view of the actuator of FIG. 1, showing the position of the components of the actuator when the knife is extended.

Referring now to FIGS. 14–16, the control knob 122 is independently connected to the plunger 118 and a knife 140 housed therein. In the preferred implementation, the control knob 122 slides along a portion of the shaft 110 in a carriage 125, as shown in FIG. 14. The control knob 122 is prevented from moving in the carriage 125 by the biasing means 124. The carriage 125 is connected to the plunger 118. Therefore a movement of the carriage 125 results in a corresponding movement of the plunger 118. When the carriage 125 has met the stop 132, any force applied by the user on the control knob 122 causes the biasing means 124 to compress, as shown in FIG. 15. This compression of the biasing means 124 allows the control knob 122 to move independently of the carriage 125. The knife 140 is connected to the control knob 122 and any further movement of the control knob 122 results in movement of the knife 140, as shown in FIG. 16. Since the knife 140 is slidable between the two insulators 142, additional movement of the control knob 122 after the carriage 125 has meet the stop 132 allows the knife 140 to extend beyond the end of the plunger 118, as shown in FIG. 9, because the knife 140 is slidable between the two insulators 142. When in the retracted position, the biasing means maintains the knife 140 in a position between the two insulators. This insures that the knife 140 will not inadvertently cut tissue which comes in contact with the headpiece.

Figure 10:
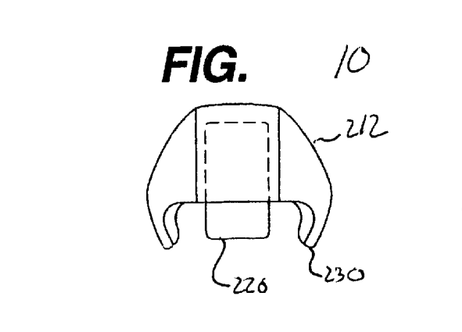
FIG. 10 illustrates an enlarged front view of an alternative headpiece having a movable hook.

Upon subsequent release of the control knob 122, the knife 140 is retracted into the plunger 118 by the force of the biasing means as shown in FIG. 10. However, the biasing means 124 preferably does not move the plunger 118 in relation to the hook 126, as can be seen in a comparison of FIGS. 15 and 16. Movement of the plunger 118 is performed by movement of the control knob 122 in the proximal direction 150 by the user which acts on the carriage 125 to move the plunger 118, as shown in FIG. 14.

Figure 5:
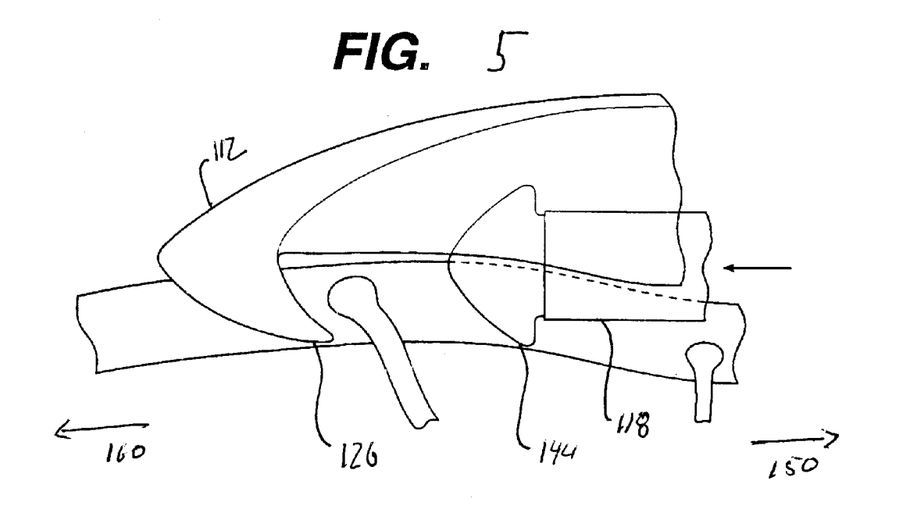
FIG. 5 illustrates an enlarged side view of a distal end of the headpiece for the endoscopic harvesting device of FIG. 1 in which a plunger is being extended.
Figure 6:
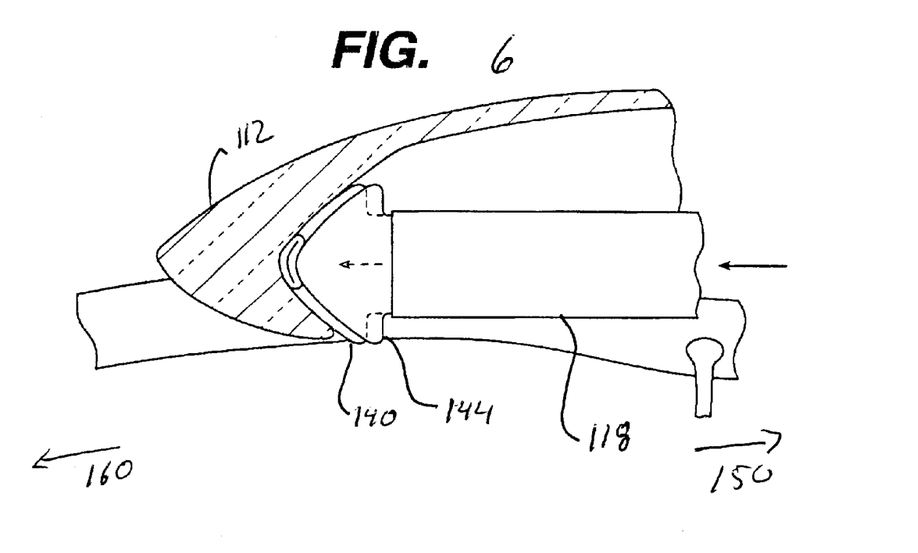
FIG. 6 illustrates an enlarged side view of a distal end of the headpiece for the endoscopic harvesting device of FIG. 1 in which a knife is extended from the plunger.

The capture, ligation and transection of a side branch vessel is as performed as follows. The operator of EVH 100 hooks a side branch vessel with the hook 126, as shown in FIG. 5. Upon hooking the vessel, the plunger 118 is extended compressing the vessel between the plunger 118 and the hook 126, as shown in FIG. 6. The electrodes 144 are then energized with RF energy, cauterizing the vessel. Then the knife 140 is extended, cutting the cauterized vessel.

Referring now to FIGS. 10–13, in an alternative configuration, the portion of the headpiece which interacts with the plunger comprises a hook 226 which is slidably engaged with the headpiece 212. In this configuration the hook 226 is connected to a control rod 244. The hook 226 is formed preferably of a medical grade thermoplastic or elastomer. The control rod 244 is actuated by an actuation means (not shown). Since it is preferable that the control rod is flexible to conform to the shape of the head piece 212, the control rod is preferably formed of a medical grade material, such as high density polyethylene.

Figure 11:
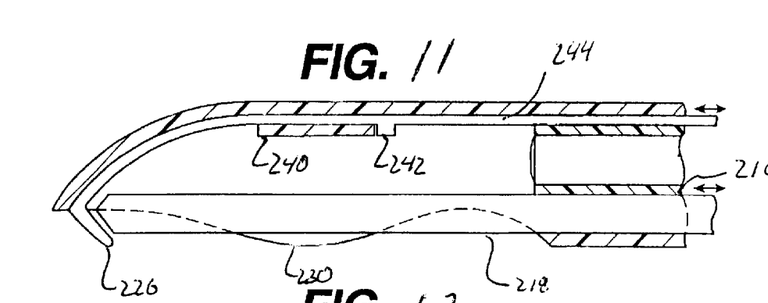
FIG. 11 illustrates an enlarged sectional side view of the headpiece of FIG. 10 having the movable hook extended.
Figure 12:
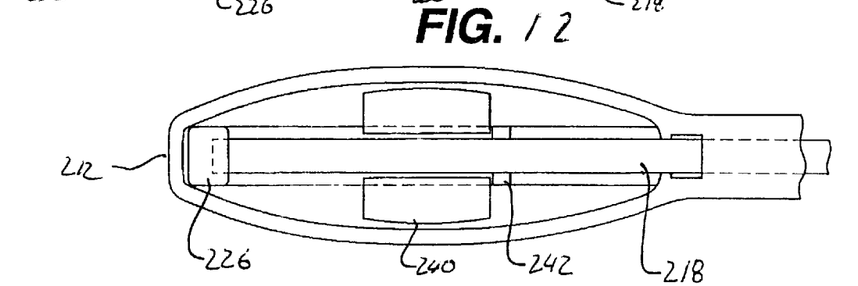
FIG. 12 illustrates an enlarged bottom view of FIG. 11.

As shown in FIGS. 11 and 12, the control rod 244 has a stop 242 which prevents the hook 226 from extending beyond the end of the headpiece 212. The stop 242 stops the movement of the control rod 244 upon coming in contact with capturing means 240. The capturing means 240 limits the travel of the control rod 244, and thereby limit the travel of the hook 226.

Figure 13:
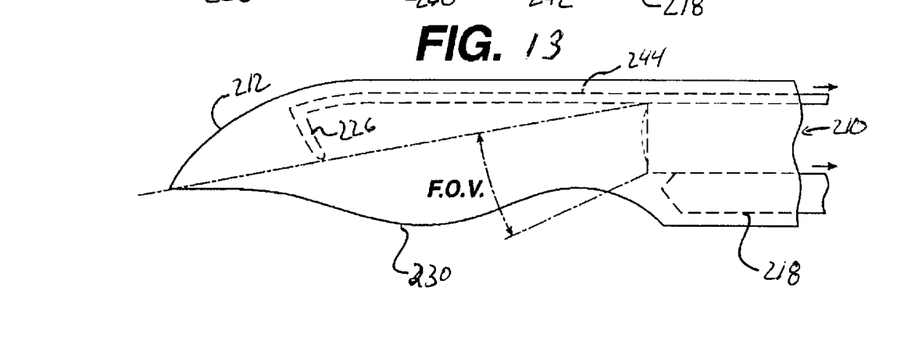
FIG. 13 illustrates an enlarged side view of the headpiece of FIG. 11 having the movable hook retracted.

Referring to FIG. 13, the capturing means 240 also prevents the control rod 244 and hook 226 assembly from entering the workspace. The capturing means 240 insures that the control rod 244 and the hook 226 follow the contours of the headpiece 212 and do not block the field of view (F.O.V.) for the endoscope 216, as shown in FIG. 16.

As shown in FIG. 11, the slidable hook 226 is also used for the ligation and transection of side branch vessels. Upon discovery of a side branch vessel, the hook 226 is slid towards the distal end 161 of the headpiece 212 using the control rod 244. Upon reaching the stop 242 the hook 226 is properly positioned, as shown in FIG. 11. The hook 226 is used to capture the side branch vessel and a plunger 218 is extended. The device preferably comprises similar ligation and transection means as that described above, and their descriptions are therefore not reiterated here. After transection, the hook 226 can then be retracted as shown in FIG. 13, to insure that it is not impeding the F.O.V. of the endoscope.

The traditional method for the removal of the saphenous vein is well known in the art. Initially, an incision is made in the patients leg. The incision is typically three or four cm in length and provides access to the vessel. The vessel is surrounded by tissue from which it must be dissected. This is accomplished using the edge of the headpiece of the harvesting device. This allows the vessel to be accessed by the harvesting device and through the dissection the head provides a workspace to continue the dissection and proceed with removal of the vessel. During the dissection process, the surgeon will uncover numerous side branch vessels which are attached to the saphenous vein. Each of these side branch vessels must be individually dissected, ligated and transected so that the saphenous vein may be removed.

A method of removing the saphenous vein using the EVH 100 as described above will now be discussed with reference to the Figures. Those skilled in the art will appreciate that the methods of the present invention limit the number of extraneous tools which must be inserted into the same incision.

The method includes the steps of locating the vessel to be removed, making an incision, and inserting the EVH 100 into the incision. The blunt dissection of the vessel is performed by moving the headpiece 112 of the EVH 100 along the vessel. This separates the vessel from tissue above the vessel and exposes the vessel to the EVH 100. Once the vessel is exposed, and separated from the surrounding tissue, a workspace 127 is defined by the headpiece 112. The workspace provides a location for the plunger 118 to be operated, shown in FIGS. 5, 6, and 11.

The vessel will undoubtedly have a number of side branch vessels connected to it. Each of these will have to be individually ligated and transected before removal of the vessel. Upon the exposing of a side branch vessel the headpiece 112 can be placed over the side branch as shown in FIG. 5.

With the headpiece 112 over the side branch the EVH 100 can be drawn back towards the operator so that the vessel can be captured by the hook 126, as shown if FIG. 5. The plunger 118 is moved in the distal direction 160 by moving control knob 122 towards the distal end 161 of the EVH 100. Upon the plunger 118 meeting the hook 126 the vessel is captured, as shown in FIG. 6. In the alternate configuration discussed above, the hook 226 is first extended before the vessel is captured.

The captured vessel is then compressed by the pressure applied by the plunger in the distal 160 direction. The side branch vessel is sandwiched between the hook and the plunger 118.

The plunger vessel 118 may also be fitted with transection and ligation means, as show in FIGS. 7 and 8. These means are actuated by the operator using their respective controls. The surgeon can actuate the ligation means, which are preferably a pair of electrodes, by energizing the electrodes 144 with RF energy via a switch (not shown) located in the handle 114 of the EVH 100 or by using a foot pedal (not shown) as is common in the art. With the plunger 118 extended and the side branch vessel captured between the hook 126 and the plunger 118, as shown in FIG. 6, RF energy can be supplied to the electrodes 144. This effectively ligates the side branch vessel by cauterization.

After the side branch vessel is ligated it can be transected. The side branch vessel can be transected using a knife edge 140 located in the plunger 118 between the insulators 142, as shown in FIG. 8. This knife 140 is actuated by moving control knob 122 in the carriage 125 in the distal 160 direction to overcome the force of the biasing means 124, as shown in FIGS. 14–16. This movement exposes the knife 140 and transects the compressed and cauterized side branch captured between the plunger 118 and the hook 126. Upon transection of the side branch vessel the surgeon can proceed with the dissection of the vessel and move to the next side branch vessel requiring ligation and transection.

Those skilled in the art will appreciate that the methods of the present invention do not require the insertion of any extraneous tools to perform the transection and ligation procedure. Nor do they require multiple tool exchanges. Accordingly, the procedure as a whole is far easier, and efficient that those previously known. As a result the stress on the patient is reduced.

Although only a few exemplary embodiments of this invention have been described in detail above, those skilled in the art will readily appreciate that many modifications are possible without materially departing from the novel teachings and advantages of this invention. Accordingly, all such modification are intended to be included within the scope of this invention as defined in the following claims.

EXAMPLE

As discussed above, the present invention has particular utility in a coronary artery bypass graft procedure (CABG), however, the use of the instruments of the present invention is now described with regard to the CABG procedure by way of example only and not to limit the scope or spirit of the present invention. A patient is prepared for cardiac surgery in a conventional manner using conventional techniques and procedures. The patient is then anesthetized and ventilated using conventional techniques. A conventional CABG procedure is performed by harvesting the greater saphenous vein from one or both of the patient's legs. The surgeon prepares an opening to the heart by dividing the patient's sternum (conventional median sternotomy) and spreading the rib cage apart using a surgical retractor. The surgeon next begins dissecting the internal mammary artery (IMA) from the chest wall of the patient, so that the distal end of the vessel may be anastomosed to the diseased lower anterior descending (LAD) coronary artery on the distal side of a lesion on the septum near the left ventricle of the heart as a source of oxygenated blood. During the surgical procedure, the surgeon optionally elects to have the patient's heart beating to perform a conventional beating heart CABG, although the surgeon has a cardiopulmonary bypass machine (CPB) primed with the patient's blood and available if it is necessary to convert the beating heart procedure into a conventional stopped heart procedure.

The surgeon prepares the heart for attaching the graft vessels by cutting and pulling away the pericardium. After checking the graft vessels for patency, collateral damage and viability, the surgeon prepares to do the anastomoses necessary to bypass the lesions in the coronary arteries. The surgeon sutures the proximal end of each graft vessel to the patient's aorta and the distal end to the diseased coronary artery, distal to the blockage or lesion. The distal end of the LAD is similarly anatomosed to a coronary artery distal to a lesion in a conventional manner. The surgeon checks the bypass grafts for adequate blood flow in a conventional manner, and then completes the remainder of the operation in a conventional manner.

The veins used in the CABG procedure are harvested endoscopically using the vein harvesting instruments of the present invention. Using these instruments, initially the patient's leg is positioned to be slightly bent and is turned to expose the inner leg. A marker is used to show on the skin the location of the vein to be harvested. Then an incision is created on the inner leg near the knee, through the skin and subcutaneous layers. The vein typically lies directly beneath the subcutaneous layers and so a middle portion of the vein is accessed through the incision. After some initial dissection with conventional blunt dissectors around this portion of the vein, a surgical instrument is introduced into the incision. An endoscope provides visualization of the vein and surrounding tissue within the working space inside the head. The instrument is advanced along the vein. Side branches off of the vein are ligated and divided a few millimeters away from the vein, taking great care not to injure the vein in any way. The harvesting procedure continues in this manner until the vein is hemostatically isolated from surrounding tissues and blood supply along the portion to be harvested. Then stab incisions are created through the skin and subcutaneous layers at the distal and proximal ends of the vein, ligation clips are applied, and the vessel is transected in order to remove the vein from the knee incision. The harvested vein is prepared for use as grafts in a conventional manner.

What is claimed is:

1. A vessel harvesting device comprising:
    a shaft having a lumen for insertion of an endoscope therethrough;
    a headpiece defining a workspace and disposed at a distal end of the shaft;
    a handle disposed at a proximal end of the shaft;
    a plunger disposed at the distal end of the shaft and movable between a retracted and extended position, wherein in the extended position the plunger interacts with at least a portion of the headpiece to capture a vessel therebetween;
    an actuation means for moving the plunger between the retracted and extended positions; and
    a ligation means for cauterizing the vessel captured between the plunger and the portion of the headpiece.

2. The vessel harvesting device as claimed in claim 1, further comprising a transection means for transecting the cauterized vessel.

3. The vessel harvesting device as claimed in claim 1, wherein the portion of the headpiece comprises a hook projecting into the workspace.

4. The vessel harvesting device as claimed in claim 1, wherein the headpiece comprises side projections extending from an edge of the headpiece and projecting towards the plunger of the headpiece, the side projections facilitating the positioning of the vessel for capture, and for dissecting around the vessel.

5. The vessel harvesting device as claimed in claim 2, wherein the ligation means comprises the plunger having at least two electrodes of opposite polarity separated by at least one dielectric layer, the electrodes being energized with RF energy to cauterize the captured vessel.

6. The vessel harvesting device as claimed in claim 5, wherein the transection means comprises the plunger having an extendable knife separated from each of the at least two electrodes by a dielectric layer.

7. The vessel harvesting device as claimed in claim 6, wherein the at least two electrodes comprises a first and second electrode and one of the first and second electrodes is a knife separated from the other electrode by at least one dielectric layer.

8. The vessel harvesting device as claimed in claim 1, wherein the portion of the headpiece comprises a slidable hook projecting into the workspace, movable from an extended to a retracted position, wherein the hook interacts with the plunger to capture the side branch when in the extended position.

9. The vessel harvesting device as claimed in claim 8, further comprising a control rod actuation means for moving the slidable hook between the extended and retracted positions.

10. The vessel harvesting device as claimed in claim 9, wherein the control rod actuation means comprises a flexible control rod operably connected to the slidable hook for sliding the slidable hook between the extended and retracted positions, the control rod having an extension stop which limits the travel of the slidable hook and also having a capturing means which prevents the slidable hook and the control rod from entering the workspace.

11. The vessel harvesting device as claimed in claim 10, wherein the control rod is formed of a flexible material conforming to the shape of the headpiece while transitioning from the retracted to the extended position and maintaining its conformance with the headpiece when in the extended position.

12. A method of harvesting a vessel comprising:
    providing a vessel harvesting device comprising a shaft having a lumen for insertion of an endoscope therethrough, a transparent headpiece defining a workspace and disposed at a distal end of the shaft, a handle disposed at a proximal end of the shaft, a plunger disposed at the distal end of the shaft and movable between a retracted and extended position, wherein in the extended position the plunger interacts with at least a portion of the headpiece to capture a vessel therebetweeen, an actuation means for moving the plunger between the retracted and extended positions, a ligation means for cauterizing the side branch, and a transection means for transecting the cauterized side branch;
    locating a vessel to be harvested;
    making an incision to expose a portion of the vessel;
    inserting the vessel harvesting device into the patient through the incision;
    dissecting the vessel from the surrounding tissue with the vessel harvesting device to expose a side branch of the vessel;
    actuating the plunger in the distal direction to capture the side branch between the plunger and the portion of the headpiece;
    applying RF energy to cauterize the captured side branch;
    transecting the cauterized side branch using the transection means;
    ligating and transecting at the proximal and distal ends of the vessel; and removing the vessel.

13. The method of harvesting a vessel as claimed in claim 12, wherein the ligating of the side branch comprises applying RF energy to the side branch using first and second electrodes, wherein the first and second electrodes are of different polarity and are housed in the plunger.

14. The method of harvesting vessels as claimed in claim 12, wherein the transecting of the side branch comprises extending a knife housed in the plunger towards the distal end of the device.

15. The method of harvesting vessels as claimed in claim 12, wherein the capturing comprises placing the headpiece over the side branch and extending the plunger in the distal direction to allow the side branch to be compressed between the plunger and the portion of the headpiece.

16. The method of harvesting vessels as claimed in claim 12, wherein the transecting of the side branch comprises advancing a knife housed in the lower jaw towards the distal end of the device subsequent to the ligation of the side branch vessel.

17. The method of harvesting vessels as claimed in claim 13, wherein the actuating comprises extending a slidable hook in the distal direction prior to extension of the plunger.

* * * * *